United States Patent
Beselt et al.

(10) Patent No.: US 9,354,090 B2
(45) Date of Patent: May 31, 2016

(54) SCANNING SENSOR ARRANGEMENT FOR PAPER MACHINES OR OTHER SYSTEMS

(71) Applicant: HONEYWELL ASCa, Inc., Mississaugo (CA)

(72) Inventors: Ronald E. Beselt, Burnaby (CA); Cristian Andronic, Burnaby (CA); Michael J. Wardas, North Vancouver (CA); Stuart James Heath, Surrey (CA); Bradley Humble, Vancouver (CA)

(73) Assignee: Honeywell Limited, Ontario (CA)

( * ) Notice: Subject to any disclaimer, the term of this patent is extended or adjusted under 35 U.S.C. 154(b) by 368 days.

(21) Appl. No.: 13/900,144

(22) Filed: May 22, 2013

(65) Prior Publication Data
US 2014/0345397 A1    Nov. 27, 2014

(51) Int. Cl.
*G01D 11/30*      (2006.01)
*G01N 21/89*      (2006.01)
*D21G 9/00*       (2006.01)

(52) U.S. Cl.
CPC .............. *G01D 11/30* (2013.01); *D21G 9/0009* (2013.01); *G01N 21/8901* (2013.01)

(58) Field of Classification Search
CPC ..... D21G 9/0009; D21G 9/0045; D21G 9/00; D21G 7/003; G01N 33/346; G01N 21/86; G01N 23/16; G01N 2021/8663; G01N 21/3554; G01N 21/5911; G01N 21/89; G01N 21/8903; G01N 21/894; G01N 2201/101; G01N 27/20; G01N 29/14; G01N 33/34; G01N 33/36
See application file for complete search history.

(56) References Cited

U.S. PATENT DOCUMENTS

| | | | | | |
|---|---|---|---|---|---|
| 3,296,710 | A | * | 1/1967 | Krikorian | 34/95 |
| 3,552,203 | A | * | 1/1971 | Freeh | 73/159 |
| 3,574,261 | A | * | 4/1971 | Bailey | 34/465 |
| 3,879,607 | A | * | 4/1975 | Bjorklund | 250/252.1 |
| 3,886,371 | A | * | 5/1975 | Lloyd | 382/321 |
| 4,000,402 | A | * | 12/1976 | Higham | 700/129 |

(Continued)

FOREIGN PATENT DOCUMENTS

| | | |
|---|---|---|
| CA | 2788122 A1 | 3/2013 |
| CN | 202220309 U | 5/2012 |
| FR | 2660491 A1 | 10/1991 |

OTHER PUBLICATIONS

International Search Report dated Jul. 30, 2014 in connection with International Patent Application No. PCT/CA2014/000412, 3 pages.

(Continued)

*Primary Examiner* — David A Rogers (57) ABSTRACT

A system includes a frame having multiple separate supports and multiple flexible rails. Each support is configured to be secured in a position apart from another support, and each flexible rail is configured to be coupled to the supports and placed under tension. The system also includes a sensor head configured to be mounted on the rails and to move back and forth along the rails. The sensor head is substantially self-contained and configured to receive operating power over the rails. The frame may further include a tensioned member configured to be coupled to the supports, and the sensor head can be configured to move back and forth using the tensioned member. The sensor head can be self-contained in that the sensor head does not push and pull any wiring assembly during movement along the rails.

23 Claims, 5 Drawing Sheets

(56) References Cited

U.S. PATENT DOCUMENTS

| | | | | |
|---|---|---|---|---|
| 4,134,781 | A * | 1/1979 | Carstens et al. | 156/64 |
| 4,245,259 | A * | 1/1981 | Pick | 358/474 |
| 4,271,699 | A * | 6/1981 | Williamson | 73/159 |
| 4,314,868 | A * | 2/1982 | Hirakawa et al. | 156/207 |
| 4,575,299 | A * | 3/1986 | Layton et al. | 414/222.05 |
| 4,575,628 | A * | 3/1986 | Bankart et al. | 250/235 |
| 4,733,078 | A * | 3/1988 | Sturm | 250/339.1 |
| 4,879,471 | A * | 11/1989 | Dahlquist | 250/359.1 |
| 5,049,216 | A * | 9/1991 | Shead et al. | 156/64 |
| 5,327,770 | A * | 7/1994 | Hindle | 73/863 |
| 5,338,361 | A * | 8/1994 | Anderson et al. | 118/689 |
| 5,663,565 | A * | 9/1997 | Taylor | 250/339.11 |
| 5,773,714 | A | 6/1998 | Shead | |
| 5,821,536 | A * | 10/1998 | Pettit | 250/339.1 |
| 6,053,040 | A * | 4/2000 | Callender et al. | 73/159 |
| 6,068,408 | A | 5/2000 | Mutoh et al. | |
| 6,655,195 | B2 * | 12/2003 | Grabscheid et al. | 73/73 |
| 6,743,337 | B1 * | 6/2004 | Ischdonat | 162/198 |
| 6,813,542 | B2 | 11/2004 | Peshkin et al. | |
| 6,832,864 | B2 * | 12/2004 | Patton | B41J 11/008 33/18.1 |
| 6,895,811 | B2 * | 5/2005 | Carey et al. | 73/159 |
| 6,907,317 | B2 | 6/2005 | Peshkin et al. | |
| 7,120,508 | B2 | 10/2006 | Peshkin et al. | |
| 7,148,499 | B2 | 12/2006 | Lapstun et al. | |
| 7,235,890 | B1 * | 6/2007 | Jasinski | 290/1 R |
| 7,567,822 | B2 | 7/2009 | Hart et al. | |
| 7,599,582 | B2 * | 10/2009 | Beselt et al. | 385/13 |
| 7,678,233 | B2 * | 3/2010 | Beselt | 162/263 |
| 7,819,034 | B2 | 10/2010 | Jasinski | |
| 7,872,574 | B2 | 1/2011 | Betts et al. | |
| 7,949,433 | B2 | 5/2011 | Hern et al. | |
| 8,101,047 | B2 * | 1/2012 | Kulma et al. | 162/181.2 |
| 8,104,363 | B2 * | 1/2012 | Kinoshita | 73/865.8 |
| 8,219,025 | B2 | 7/2012 | Andronic | |
| 8,561,468 | B2 * | 10/2013 | Beselt et al. | 73/570 |
| 8,573,834 | B2 | 11/2013 | Bik | |
| 8,979,258 | B2 | 3/2015 | Usuda | |
| 9,004,638 | B2 | 4/2015 | Wakayama et al. | |
| 2002/0104637 | A1 * | 8/2002 | Koivukunnas et al. | 162/263 |
| 2004/0182594 | A1 * | 9/2004 | Chen et al. | 174/100 |
| 2004/0221978 | A1 * | 11/2004 | Tran et al. | 162/198 |
| 2005/0192710 | A1 | 9/2005 | Thornton et al. | |
| 2006/0243931 | A1 | 11/2006 | Haran et al. | |
| 2006/0254367 | A1 * | 11/2006 | Hellstrom | 73/828 |
| 2007/0039705 | A1 * | 2/2007 | Stewart | 162/198 |
| 2007/0058212 | A1 * | 3/2007 | Beselt et al. | 358/474 |
| 2008/0129495 | A1 | 6/2008 | Hitt | |
| 2009/0099682 | A1 * | 4/2009 | Jasinski | 700/128 |
| 2009/0229777 | A1 * | 9/2009 | Tran et al. | 162/198 |
| 2009/0242157 | A1 * | 10/2009 | Heintz et al. | 162/263 |
| 2009/0258604 | A1 * | 10/2009 | Andronic | 455/73 |
| 2011/0284178 | A1 * | 11/2011 | Shakespeare | 162/198 |
| 2011/0290438 | A1 * | 12/2011 | Chu et al. | 162/198 |
| 2013/0055912 | A1 | 3/2013 | Beselt et al. | |
| 2014/0320857 | A1 | 10/2014 | Then et al. | |
| 2014/0348154 | A1 | 11/2014 | Hofman et al. | |

OTHER PUBLICATIONS

Written Opinion of International Searching Authority dated Jul. 30, 2014 in connection with International Patent Applicatoin No. PCT/CA2014/000412, 4 pages.

Tom Rosenberg, Product Line Manager, Balluff Inc., Understanding non-contact transmission of power and sensor signals, Design News, Jun. 1, 2001, www.designnews.com, 7 pages.

Cristian Andronic, et al.; U.S. Appl. No. 13/900,190 titled "Power Delivery System for Providing Power to Sensor Head of Paper Machine or Other System" filed May 22, 2013; 29 pages.

Prasad Samudrala, et al. ;U.S. Appl. No. 13/871,897 titled "Slot Segregation for Supporting Multiple Communication Protocols in an Industrial Wireless Network" filed Apr. 26, 2013; 29 pages.

Non-Final Office Action dated Jul. 9, 2015 in connection with U.S. Appl. No. 13/900,190; 9 pages.

* cited by examiner

SCANNING SENSOR ARRANGEMENT FOR PAPER MACHINES OR OTHER SYSTEMS

TECHNICAL FIELD

This disclosure relates generally to scanning systems. More specifically, this disclosure relates to a scanning sensor arrangement for paper machines or other systems.

BACKGROUND

Sheets or other webs of material are used in a variety of industries and in a variety of ways. These materials can include paper, multi-layer paperboard, and other products manufactured or processed in long webs. As a particular example, long sheets of paper can be manufactured and collected in reels.

It is often necessary or desirable to measure one or more properties of a web of material as the web is being manufactured or processed. Adjustments can then be made to the manufacturing or processing system to ensure that the properties stay within desired ranges. Measurements are often taken using scanners that move sensor heads containing sensors back and forth across the width of the web.

Scanners that are used in web manufacturing or processing systems often represent large structures with various components distributed throughout the structures. Unfortunately, a scanner typically cannot be tested until its various components are collected and assembled together into a complete functional unit. This often requires extensive time in a factory to ensure that all components (which have varying lead times) are available in the same factory location for testing as an integrated unit prior to shipment to a customer.

SUMMARY

This disclosure provides a scanning sensor arrangement for paper machines or other systems.

In a first embodiment, a system includes a frame having multiple separate supports and multiple flexible rails. Each support is configured to be secured in a position apart from another support, and each flexible rail is configured to be coupled to the supports and placed under tension. The system also includes a sensor head configured to be mounted on the rails and to move back and forth along the rails. The sensor head is substantially self-contained and configured to receive operating power over the rails.

In a second embodiment, an apparatus includes a scanner frame having multiple separate supports and multiple flexible rails. Each support is configured to be secured in a position apart from another support. Each flexible rail is configured to be coupled to the supports and placed under tension, and the rails are configured to support a sensor head when under tension.

In a third embodiment, an apparatus includes a sensor head configured to be mounted on rails of a scanner frame and to move back and forth along the rails. The sensor head is substantially self-contained and is configured to receive operating power over the rails.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 7, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
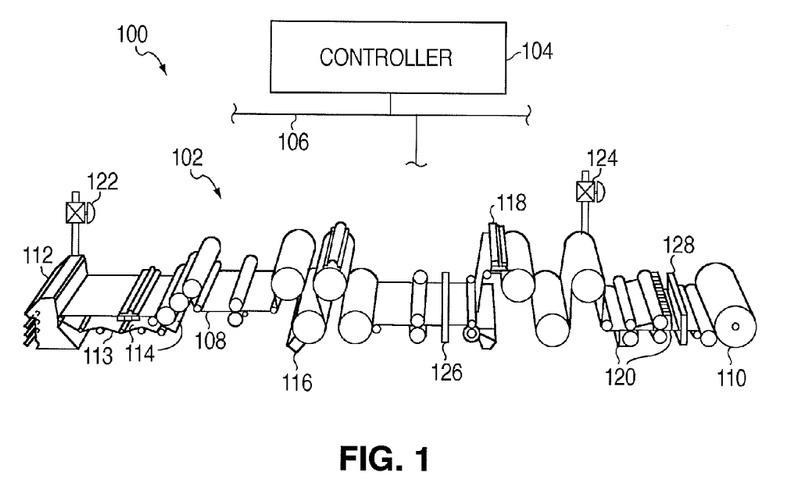
FIG. 1 illustrates an example web manufacturing or processing system according to this disclosure.

FIG. 1 illustrates an example web manufacturing or processing system 100 according to this disclosure. In this example, the system 100 includes a paper machine 102, a controller 104, and a network 106. The paper machine 102 includes various components used to produce a paper product, namely a paper web 108 that is collected at a reel 110. The controller 104 monitors and controls the operation of the paper machine 102, which may help to maintain or increase the quality of the paper web 108 produced by the paper machine 102.

In this example, the paper machine 102 includes at least one headbox 112, which distributes a pulp suspension uniformly across the machine onto a continuous moving wire screen or mesh 113. The pulp suspension entering the headbox 112 may contain, for example, 0.2-3% wood fibers, fillers, and/or other materials, with the remainder of the suspension being water. The headbox 112 may include an array of dilution actuators, which distributes dilution water into the pulp suspension across the web. The dilution water may be used to help ensure that the resulting paper web 108 has a more uniform basis weight across the web 108.

Arrays of drainage elements 114, such as vacuum boxes, remove as much water as possible to initiate the formation of the web 108. An array of steam actuators 116 produces hot steam that penetrates the paper web 108 and releases the latent heat of the steam into the paper web 108, thereby increasing the temperature of the paper web 108 in sections across the web. The increase in temperature may allow easier removal of remaining water from the paper web 108. An array of rewet shower actuators 118 adds small droplets of water (which may be air atomized) onto the surface of the paper web 108. The array of rewet shower actuators 118 may be used to control the moisture profile of the paper web 108, reduce or prevent over-drying of the paper web 108, or correct any dry streaks in the paper web 108.

The paper web 108 is then often passed through a calender having several nips of counter-rotating rolls. Arrays of induction heating actuators 120 heat the shell surfaces of various ones of these rolls. As each roll surface locally heats up, the roll diameter is locally expanded and hence increases nip pressure, which in turn locally compresses the paper web 108. The arrays of induction heating actuators 120 may therefore be used to control the caliper (thickness) profile of the paper web 108. The nips of a calender may also be equipped with other actuator arrays, such as arrays of air showers or steam showers, which may be used to control the gloss profile or smoothness profile of the paper web.

Two additional actuators 122-124 are shown in FIG. 1. A thick stock flow actuator 122 controls the consistency of incoming stock received at the headbox 112. A steam flow actuator 124 controls the amount of heat transferred to the paper web 108 from drying cylinders. The actuators 122-124 could, for example, represent valves controlling the flow of stock and steam, respectively. These actuators 122-124 may be used for controlling the dry weight and moisture of the paper web 108.

Additional components could be used to further process the paper web 108, such as a supercalender (for improving the paper web's thickness, smoothness, and gloss) or one or more coating stations (each applying a layer of coatant to a surface of the paper to improve the smoothness and printability of the paper web). Similarly, additional flow actuators may be used to control the proportions of different types of pulp and filler material in the thick stock and to control the amounts of various additives (such as retention aid or dyes) that are mixed into the stock.

This represents a brief description of one type of paper machine 102 that may be used to produce a paper product. Additional details regarding this type of paper machine 102 are well-known in the art and are not needed for an understanding of this disclosure. Also, this represents one specific type of paper machine 102 that may be used in the system 100. Other machines or devices could be used that include any other or additional components for producing a paper product. In addition, the control system described below is not limited to use with systems for producing paper products and could be used with systems that process a paper product or with systems that produce or process other items or materials (such as multi-layer paperboard, cardboard, plastic, textiles, metal webs, or other or additional materials that are manufactured or processed as moving webs).

In order to control the paper-making process, one or more properties of the paper web 108 may be continuously or repeatedly measured. The web properties can be measured at one or various stages in the manufacturing process. This information may then be used to adjust the paper machine 102, such as by adjusting various actuators within the paper machine 102. This may help to compensate for any variations of the web properties from desired targets, which may help to ensure the quality of the web 108.

As shown in FIG. 1, the paper machine 102 includes one or more scanners 126-128, each of which may include one or more sensors. Each scanner 126-128 is capable of measuring one or more characteristics of the paper web 108. For example, each scanner 126-128 could include sensors for measuring the caliper, anisotropy, basis weight, color, gloss, sheen, haze, surface features (such as roughness, topography, or orientation distributions of surface features), or any other or additional characteristics of the paper web 108.

Each scanner 126-128 includes any suitable structure or structures for measuring or detecting one or more characteristics of the paper web 108. For example, each scanner 126-128 could include one or more sets of sensors mounted on a sensor head that moves back and forth across the web 108. Note, however, that stationary sensors could also be used at one or more locations of the paper machine 102.

The controller 104 receives measurement data from the scanners 126-128 and uses the data to control the paper machine 102. For example, the controller 104 may use the measurement data to adjust any of the actuators or other components of the paper machine 102. The controller 104 includes any suitable structure for controlling the operation of at least part of the paper machine 102, such as a computing device.

The network 106 is coupled to the controller 104 and various components of the paper machine 102 (such as the actuators and scanners). The network 106 facilitates communication between components of the system 100. The network 106 represents any suitable network or combination of networks facilitating communication between components in the system 100. The network 106 could, for example, represent a wired or wireless Ethernet network, an electrical signal network (such as a HART or FOUNDATION FIELDBUS network), a pneumatic control signal network, or any other or additional network(s).

As described in more detail below, at least one of the scanners 126-128 can include the following features. First, a scanner can include a frame that lacks horizontal support beams extending across the length of the scanner. Instead, the frame can include separate supports anchored on opposite sides of the scanner, along with flexible rails coupled to the supports and placed under tension. Second, a scanner can include one or more sensor heads that are substantially self-contained, meaning the sensor head is not required to push and pull wiring assembly during operation. Instead, power can be provided to each sensor head via two or more rails, and wireless communications can be used to interact with the sensor head(s). Third, each sensor head can include a drive system for moving each sensor head back and forth in the scanner using a tensioned cable or other member under tension.

In this way, the frame of a scanner may include two supports and several flexible rails and cables coupling the supports. As a result, the frame can be manufactured and assembled more easily. Also, each sensor head can be manufactured and tested separate from the frame. For example, most or all of the scanning functionality of a sensor head can be tested using a standard "dumb" frame at the sensor head manufacturer's facility. The sensor head need not be tested with the actual frame to be used in a particular installation of a scanner. In addition, because the overall scanner is formed from smaller pieces and does not include a large fixed frame, the scanner can be broken down and shipped in a smaller space (possibly even on a single standard-size pallet).

Additional details regarding possible implementations of a scanner are provided below. Note that while a scanner may be described as having all three of the features described above, it is possible for a scanner to implement a single feature or a combination of any two features described above.

Although FIG. 1 illustrates one example of a web manufacturing or processing system 100, various changes may be made to FIG. 1. For example, other systems could be used to produce other paper or non-paper products. Also, while shown as including a single paper machine 102 with various components and a single controller 104, the system 100 could include any number of paper machines or other machinery having any suitable structure, and the system 100 could include any number of controllers. In addition, FIG. 1 illustrates one operational environment in which a scanner can be used. A scanner could be used in any other type of system, and that system need not manufacture or process moving webs or webs.

Figure 2:
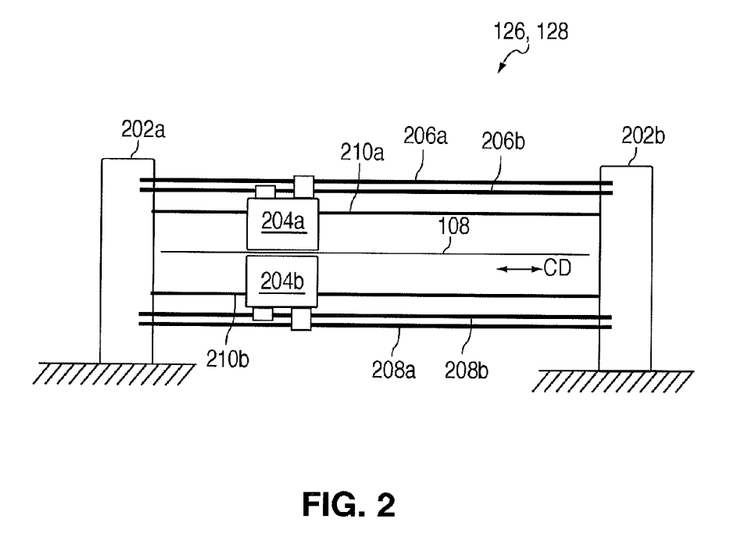
FIGS. 2 through 6 illustrate an example scanner and related details for a paper machine or other system according to this disclosure.

FIGS. 2 through 6 illustrate an example scanner 126, 128 and related details for a paper machine or other system according to this disclosure. As shown in FIG. 2, the scanner includes two supports 202a-202b on opposite sides of the scanner. Each support 202a-202b generally represents a structure that can be secured in place to the ground or an external structure and to which other components of the scanner can be attached or mounted. As shown here, the supports 202a-202b are separated by a space in which the web 108 can pass. Each support 202a-202b can be formed from any suitable material(s), such as metal. Each support 202a-202b can also be formed in any suitable manner, such as welding. In addition, while shown here as being secured in place to the ground, each support 202a-202b could be secured to an external structure, such as to a frame or other component(s) of the paper machine 102.

The scanner also includes multiple sensor heads 204a-204b. Each sensor head 204a-204b generally includes one or more sensors capable of measuring at least one characteristic of a material. For example, each sensor head 204a-204b could include sensor(s) for measuring the moisture, caliper, anisotropy, basis weight, color, gloss, sheen, haze, surface features (such as roughness, topography, or orientation distributions of surface features), or any other or additional characteristic(s) of the web 108. Each sensor head 204a-204b includes any suitable structure or structures for measuring or detecting one or more characteristics of a material.

As shown in FIG. 2, the scanner here has a frame that lacks horizontal support beams extending across the length of the scanner. Scanners for flat sheet processes have been built traditionally using rigid members that form a stiff frame. The stiff frame typically includes horizontal beams on top and bottom that extend along substantially the entire length of the scanner. Rails are attached at periodic intervals to the horizontal beams, and the attachment points normally allow for adjustment of the rails relative to the frame. This allows each rail to be adjusted to define a straight path along the length of the scanner at a constant relative distance from an opposing path on the other horizontal beam. Sensor heads are mounted to the rails, and the load of each sensor head is transferred to the associated horizontal beam.

This approach is problematic for a number of reasons. Designing, constructing, and maintaining precision scanner frames are often labor-intensive efforts. For example, alignment of the rails on the frame is time-consuming, and the rails can become misaligned later if the frame distorts in shape (such as due to additional mass loads, material stress relaxation, shipping stresses, or thermal loads). Also, scanner frame construction is often specialized in both tooling and expertise, meaning scanner frames are often fabricated in a limited number of factory settings. In a worldwide market, this routinely requires long shipping distances for manufactured scanner frames. Moreover, scanner frames are typically customized in size for particular installations, so the construction of a scanner frame typically does not begin until all dimensions for a particular installation are known. This leads to an inefficient one-off manufacturing model and long cycle times. Further, since scanner frames are typically very long, shipping expenses for an assembled scanner frame can be quite high, even when the frame's width and height may not be overly large. Custom crating and special handling add to the shipping costs. Air shipments are very costly, and ground shipments add to delivery times. Finally, scanner frames for shorter processes typically utilize the same overall design and materials as scanner frames for larger processes. This leads to overbuilt designs and costs that do not scale down to match the economics of smaller applications.

In accordance with the first aspect of this disclosure, the scanner in FIG. 2 omits fixed horizontal support beams between the supports 202a-202b. Instead, the scanner uses a number of flexible rails. In the example shown in FIG. 2, at least two rails 206a-206b are coupled between the supports 202a-202b near the top of the supports 202a-202b, and at least two rails 208a-208b are coupled between the supports 202a-202b near the bottom of the supports 202a-202b. The sensor head 204a can be connected to and ride along the rails 206a-206b, and the sensor head 204b can be connected to and ride along the rails 208a-208b. The rails 206a-206b, 208a-208b are flexible and can be coiled or otherwise reduced in length for transport. The rails 206a-206b, 208a-208b can also be coupled to the supports 202a-202b and placed under tension. This allows the rails 206a-206b, 208a-208b to provide largely straight paths and support for the sensor heads 204a-204b.

As a result, the sensor heads 204a-204b can ride along their respective rails 206a-206b, 208a-208b and move back and forth across the scanner. This can be accomplished without requiring the use of fixed horizontal beams linking the supports 202a-202b. Instead, the supports 202a-202b are designed to carry tensile loads, and the rails 206a-206b, 208a-208b extend between the supports 202a-202b. In particular embodiments, this design of the scanner's frame can be used for smaller scanner spans and lower payload masses.

Among other things, this design of the scanner's frame allows the frame to be largely constructed prior to knowing the exact length of the scanner. The supports 202a-202b can be manufactured at any suitable time, and the length of the rails 206a-206b, 208a-208b can be easily tailored when the exact length of the scanner becomes known. This increases manufacturing efficiency and reduces lead time. Also, this approach allows the supports 202a-202b and the rails 206a-206b, 208a-208b to be shipped in a much smaller package compared to conventional frames with fixed horizontal support beams. This lowers shipping costs and reduces fragile handling requirements and custom crating usage. This design further allows for bulk shipment of frame components to distribution centers or other locations for final assembly onsite at customers' facilities. Moreover, this design helps to maintain sensor head alignment independent of thermal issues, shipping stresses, and other factors. In addition, this design changes the scanner frame from a complex electromechanical structure to a simpler guide path across a process, which reduces build costs and improves delivery times.

The rails 206a-206b, 208a-208b could be formed from any suitable material(s) and in any suitable manner. For example, the rails 206a-206b, 208a-208b could represent metal cables or cables formed from pultruded composite material(s). The rails can be flexible enough to be shipped in a coiled fashion or other reduced-size manner without damage. The rails can also have a suitable size to engage profiled rollers or other structures of the sensor heads 204a-204b that contact the rails. The rails can further have a finish that allows for accurate travel of the sensor heads 204a-204b, such as a generally smooth finish. In particular embodiments, each rail 206a-206b, 208a-208b could represent a stainless steel, ¼" to ½" diameter, 19×1 die-formed cable.

In this example, each sensor head 204a-204b contacts and rides on two rails. However, more than two rails could also be provided for each sensor head. For instance, three or four rails could be used for each sensor head to provide for greater torsional rigidity. Also, each support 202a-202b could include precisely-located holes that receive connectors for coupling to anchors or other portions of the rails 206a-206b, 208a-208b. This allows the supports 202a-202b to clearly and easily define the positions and spacings of the rails relative to each other.

Conventional scanners also include various subsystems such as drive mechanics, position feedback mechanics, control electronics, pneumatics, umbilical cables, data acquisition systems, and cooling systems. Traditionally, these subsystems are spread throughout the frame and sensor heads. For example, a single motor at one end of a scanner frame often drives moving belts and encoders that pull the sensor heads back and forth. Drive control electronics are often situated on the scanner frame in close proximity to the motor.

Cooling water and pneumatic power are often supplied at one end of the scanner frame and transmitted to sensor heads by umbilical cable sets in the form of cable trays. Signals from the sensor heads are sometimes sent in analog format to data acquisition electronics at one end of the scanner frame via wiring in the umbilical cable sets. Many variations exist, but conventional systems routinely spread sensor drive, environmental control, pneumatic power, sensor signal, and motion control functionality and wiring throughout the scanner frame and sensor heads.

One problem with this approach is that a scanner cannot be fully tested until its sensor heads, frame, and associated wiring and control modules are all hooked up together so that the scanner can be tested as a complete unit. This often requires extensive time in a factory to ensure that the components are all available in the same factory location for testing as an integrated unit prior to shipment to a customer.

In accordance with the second aspect of this disclosure, each sensor head 204a-204b could represent a substantially self-contained sensor head. For example, as described below, each sensor head 204a-204b could receive operating power over its respective rails 206a-206b, 208a-208b. Also, each sensor head 204a-204b could include a wireless radio for transmitting sensor measurements or other data and for receiving commands or other data. Further, each sensor head 204a-204b could include a motor or other driver for moving the sensor head 204a-204b along its respective rails. In addition, each sensor head 204a-204b could include additional components, such as a local air supply and temperature controller, that perform other functions locally within that sensor head.

The use of one or more substantially self-contained sensor heads allows numerous functions of each sensor head to be tested separate from the frame on which that sensor head will ultimately be used. In some embodiments, a sensor head can be used on a scanner frame devoid of moving belts, wiring, and hoses that travel along with the sensor head as the sensor head scans back and forth. As a result, each sensor head can be tested using a "dumb" test frame, such as a frame that simply supports sensor alignment and power transmission along electrified rails. Testing of the scanner frame used in a particular installation can therefore occur separate from testing of the sensor head(s) used in the particular installation. In fact, it is possible for a customer to obtain the scanner frame and the sensor heads from different manufacturers.

In addition, traditional scanners often use a drive system having a belt drive that is driven from a stationary motor fixed to the scanner's frame. This typically requires the use of a belt that spans two full lengths of the scanner frame since the belt travels from the motor at one end of the frame to an idler pulley at the opposite end of the frame, wraps around the idler pulley, and goes back to the motor. Also, separate belts are needed when the scanner includes sensor heads on opposite sides of a web. A multitude of parts are often needed to provide a reduction from the motor drive, split the motor's power between multiple belts, and control the routing, sag, tension, and attachment of the belts. Additional challenges arise when the belts are pulled from opposite ends of their respective runs, resulting in one sensor head having a longer pull length compared to the other sensor head and thus creating an undesirable relative offset. These relative offsets are also affected by differences in the dynamics of the upper and lower sensor heads due to mass, friction in the belt system, friction in the rolling elements that support each head, tension of the belts, and stiffness of the belts.

In accordance with the third aspect of this disclosure, each sensor head 204a-204b can include its own drive system for moving that sensor head back and forth. For example, each drive system can move its associated sensor head 204a-204b back and forth along that sensor' heads respective rails. In some embodiments, the sensor heads 204a-204b are coupled to additional tensioned members 210a-210b, respectively. Each tensioned member 210a-210b could represent a cable or other structure placed between the supports 202a-202b and that is under tension. The drive system on each sensor head 204a-204b can include a motor and various pulleys or sprockets around which the associated tensioned member 210a-210b can be placed. The motor can then turn one of the pulleys or sprockets to move the sensor head along the tensioned member 210a-210b.

Among other things, this design of the drive system allows each tensioned member 210a-210b to span one length of the scanner frame without requiring a return span. This reduces the amount of material needed by a factor of two. Also, use of a single span member equalizes the pull length of a sensor head 204a-204b. Further, components used to split power from a motor and to route belts can be eliminated, and frictional losses from belts running over idler pulleys can be reduced. This results in less power being required to drive the sensor heads, and each drive system can have fewer parts. Moreover, using a lightweight tensioned member reduces sag so that guides for controlling sag are no longer required. In addition, physical differences between upper and lower tensioned members that result in relative offsets of the sensor heads can be compensated out of the scanner through a dual motor drive control strategy.

Note that in FIG. 2 and the above description, the scanner in FIG. 2 is shown and described as having multiple sensor heads 204a-204b, one on each side of the web 108. However, other arrangements can also be used in a scanner. For example, the scanner could include multiple sensor heads on one side of the web 108. Also, the scanner could include a single sensor head on only one side of the web 108.

In addition, while the two rails 206a-206b or 208a-208b are shown here as being spaced apart, this is not required. For instance, the rails 206a-206b or 208a-208b could form part of a single rail case having an external conductive shell with at least one opening exposing an inner conductor. In this arrangement, the outer conductive shell could represent one rail, and the inner conductor could represent the other rail. Brushes or other electrical contacts could contact the outer conductive shell and the inner conductor through the opening(s) in the outer shell. Any other suitable arrangement for the rails could be used.

Figure 3:
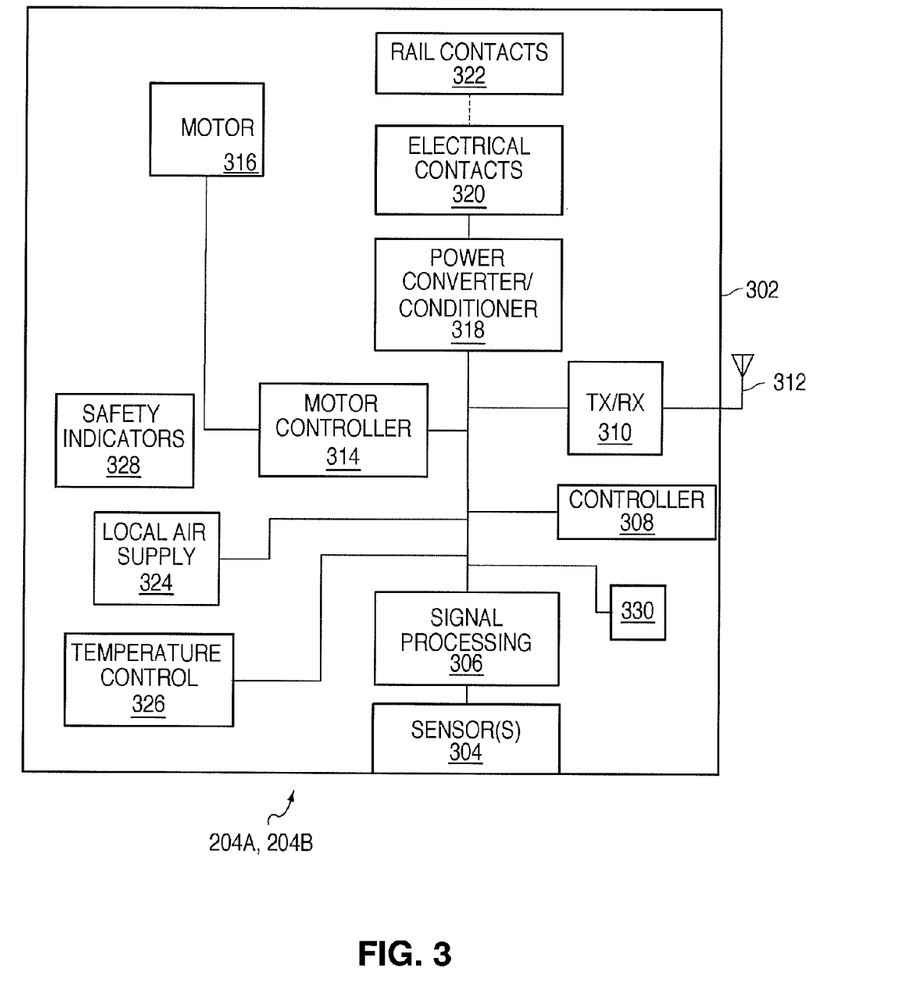

FIG. 3 illustrates additional details of an example scanning sensor head 204a, 204b. As shown in FIG. 3, the sensor head 204a, 204b includes a moveable chassis 302, which represents a housing or other structure configured to encase, contain, or otherwise support other components of the sensor head 204a, 204b. The chassis 302 can be formed from any suitable material(s) (such as metal) and in any suitable manner.

The sensor head 204a, 204b also includes one or more sensors 304 that capture measurements associated with the web 108 or other material(s). Each sensor 304 includes any suitable structure for capturing measurements associated with one or more characteristics of a material. A sensor 304 could represent a contact sensor that takes measurements of a web via contact with the web or a non-contact sensor that takes measurements of a web without contacting the web. Each sensor head 204a, 204b could include any number of sensors 304.

Signal processing circuitry 306 in the sensor head can process measurement data from the sensor(s) 304. For example, the signal processing circuitry 306 could perform signal conditioning, analog-to-digital (A/D) conversion, filtering, and position/time stamping. Other or additional functions could be performed by the signal processing circuitry 306 to process sensor measurements depending on particular needs. The position/time stamping function can associate a sensor measurement with both (i) a time at which the measurement was taken and (ii) a position of the sensor head when the measurement was taken. Additional details of one example technique for associating sensor measurements with times and positions are provided in U.S. patent application Ser. No. 13/900,738, entitled "Wireless Position-Time Synchronization for Scanning Sensor Devices" (which is hereby incorporated by reference in its entirety). The signal processing circuitry 306 includes any suitable structure(s) for processing sensor measurements.

A controller 308 controls the overall operation of the sensor head 204a, 204b. For example, the controller 308 could receive measurements from one or more sensors 304 and control wireless transmission of the sensor measurements to one or more destinations. The controller 308 includes any suitable processing or control device(s), such as one or more microprocessors, microcontrollers, digital signal processors, field programmable gate arrays, or application specific integrated circuits. Note that the controller 308 could also be implemented as multiple devices.

A wireless transceiver 310 is coupled to one or more antennas 312. The wireless transceiver 310 facilitates the wireless transmission and reception of data, such as by transmitting sensor measurements and related data to a control system and receiving commands from the control system. The wireless transceiver 310 includes any suitable structure for generating signals for wireless transmission and/or for processing signals received wirelessly. In particular embodiments, the wireless transceiver 310 represents a radio frequency (RF) transceiver. Note that the transceiver 310 could be implemented using a transmitter and a separate receiver. The antenna 312 represents any suitable structure for transmitting and receiving wireless signals, such as an RF antenna.

A motor controller 314 can be used to control the operation of a motor 316 in the sensor head 204a, 204b. The motor 316 can be used to move the sensor head 204a, 204b back and forth along the rails 206a-206b, 208a-208b. For example, the motor 316 can be used to pull on the tensioned member 210a-210b to move the sensor head back and forth. The motor controller 314 could generate and output pulse width modulation (PWM) or other control signals for adjusting the direction and speed of the motor 316. The direction and speed could be controlled based on input from the controller 308. The motor controller 314 includes any suitable structure(s) for controlling the operation of a motor. For instance, the motor controller 314 could include a motor drive, motor control electronics and processing, limit switches, a position feedback mechanism, and a head-to-head alignment mechanism. The motor 316 includes any suitable type of motor, such as a stepper motor that can be precisely controlled.

The sensor head 204a, 204b further includes a power converter/conditioner 318. The power converter/conditioner 318 is electrically connected to two or more rails 206a-206b, 208a-208b and receives electrical power from the rails. Electrical contacts 320 may be used to form electrical connections to the rails 208a-208b directly or indirectly, such as via rail contacts 322. The power converter/conditioner 318 can receive electrical power and convert the electrical power into a form suitable for use in a sensor head. For example, the power converter/conditioner 318 could receive AC power from a power supply and convert the AC power into a DC form, or the power converter/conditioner 318 could receive DC power from a power supply and convert the DC power into a different DC form. As a particular example, the power converter/conditioner 318 could receive a 20-40 VAC 50-60 Hz signal from a power supply and convert the signal into a 24 VDC signal. The power converter/conditioner 318 could also condition the received power, such as by filtering the received power (with or without also converting the form of the power). The power converter/conditioner 318 includes any suitable structure for converting power from one form to another and/or conditioning power.

Each electrical contact 320 includes any suitable structure for forming a direct or indirect electrical connection to a rail. Any suitable electrical contacts 320 can be used in a sensor head to receive operating power from two or more rails. In some embodiments, the electrical contacts 320 represent brushes, rollers, sliders, or other structures used to form electrical connections directly on the rails. In other embodiments, the electrical contacts 320 represent brushes, rollers, sliders, or other structures used against rail contacts 322 that contact the rails (such as bearing assemblies or wheels), thereby providing indirect electrical connections with the rails.

The rail contacts 322 couple the sensor head 204a, 204b to the rails 206a-206b, 208a-208b so that the sensor head can move back and forth on the rails. The rail contacts 322 can also optionally be used to provide power from the rails to the electrical contacts 320. For example, the rail contacts 322 can allow electrical currents to flow between the rails and the power converter/conditioner 318. Each rail contact 322 includes any suitable structure(s) for coupling a sensor head to a rail.

In some embodiments, each rail contact 322 includes a bearing assembly having an outer race, an inner race, bearings, and a cage. The outer race and the inner race generally form a channel in which the bearings and cage reside. The inner race can rotate independent of the outer race, and the bearings help to facilitate this rotation by rolling within the channel between the outer and inner races. The cage helps to maintain the separation of the bearings. In other embodiments, each rail contact 322 includes a bearing wheel having an outer race, an inner race, and a connector fixedly connecting the outer and inner races. In these embodiments, current could flow through the bearing assembly or wheel to an electrical contact 320. For instance, current could flow through the outer race only or through the outer race and the inner race. Note, however, that the rail contacts 322 could be implemented in any other suitable manner, such as by using sliders made of carbon, graphite, or other suitable material(s) that simply slide along the rails.

Various additional components could be used in the sensor head according to particular needs. For example, a local air supply 324 could be used to provide compressed air for sensing or other operations. The local air supply 324 could include a small compressor for compressing air and a tank for storing the compressed air. The compressor could operate based on power received by the power converter/conditioner 318. As another example, a temperature control unit 326 could be used to provide environmental temperature control for the sensor head. For instance, the temperature control unit 326 could include a heater or cooler for controlling the temperature of the sensor(s) 304. As a particular example, the temperature control unit 326 could include a thermoelectric cooler that helps to ensure sensor safety and stability. As a further example, the sensor head could include one or more safety indicators 328, such as power, temperature, or radiation indicators, that identify different conditions.

In addition, a position sensor 330 can be used to identify the position of the sensor head. The position sensor 330 could use any suitable technique to identify the position of the sensor head. For example, the position sensor 330 could include a stepper motor step counter that supports open loop position control. As another example, the position sensor 330 could receive data from a tachometer defining the rotational speed of the motor 316 or data from the motor controller 314 defining how the motor 316 is being driven. Using this data or other or additional data, the position sensor 330 can identify the sensor head's current position to support closed loop position control. The current position could be identified in any suitable form, such as an absolute location or a distance from a last-known location. The position sensor 330 includes any suitable structure for identifying the location of a sensor head.

In this way, most or all of the components needed by a sensor head to operate and capture sensor measurements are included within the sensor head itself. The sensor head may only need a frame with the appropriately-spaced rails and cables and the ability to provide power over the rails in order to operate. This can greatly simplify testing, installation, and maintenance.

Figure 4:
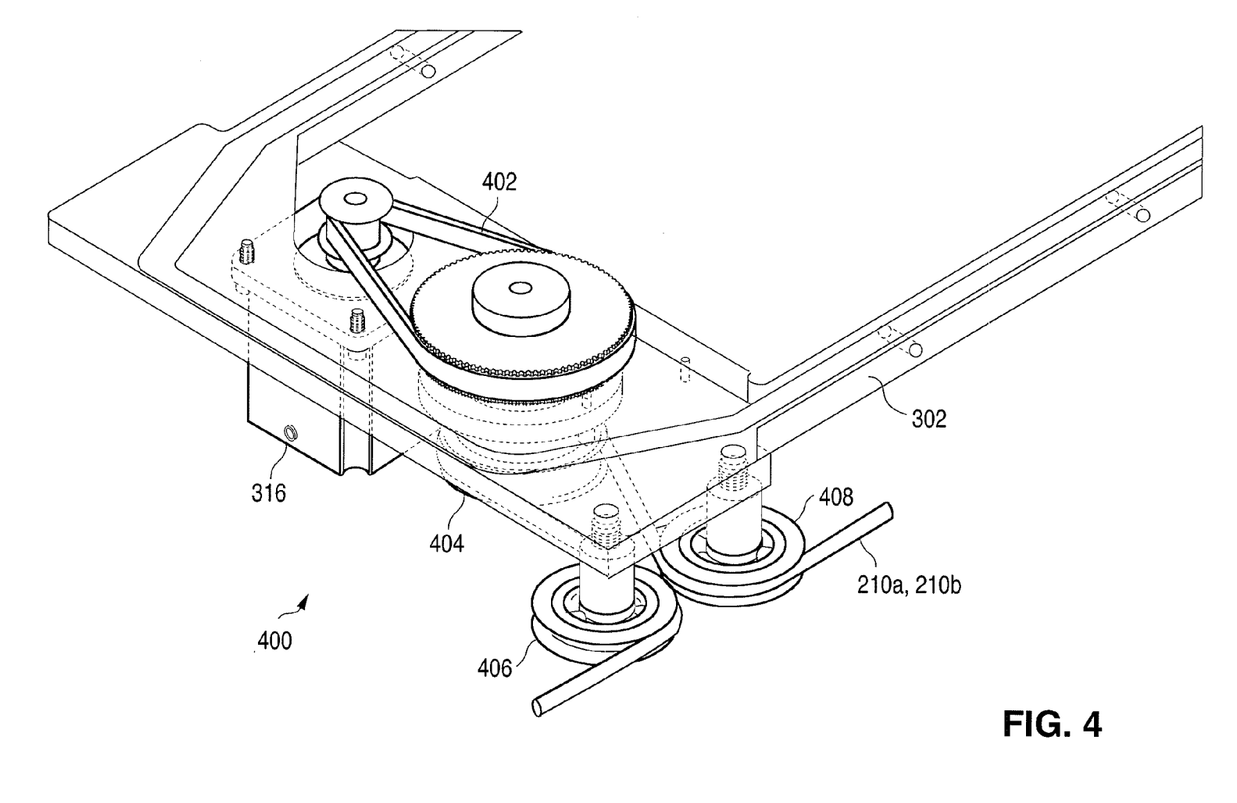

FIG. 4 illustrates an example motor assembly 400 that can be used with a sensor head 204a-204b. As shown in FIG. 4, the motor 316 is mounted on the chassis 302 of the sensor head. The motor 316 connects to a pulley reduction system 402, which translates more rapid revolutions of the motor 316 into slower revolutions of a drive pulley 404. One of the tensioned members 210a-210b wraps around two guide pulleys 406-408 and the drive pulley 404.

When the motor 316 operates, the motor 316 causes the drive pulley 404 to rotate (via its connection to the drive pulley 404 through the pulley reduction system 402). Since the guide pulleys 406-408 help to keep the tensioned member 210a-210b in contact with the drive pulley 404, rotation of the drive pulley 404 pulls on the tensioned member 210a-210b, moving the sensor head. By controlling the directional rotation of the motor 316, movement of the sensor head back and forth can be precisely controlled.

Note that the arrangement of the pulleys 404-408 is for illustration only, and other arrangements could be used. For example, the tensioned member 210a-210b contacts different percentages of the perimeters of the guide pulleys 406-408 in FIG. 4. The guide pulleys 406-408 could be centered with respect to the drive pulley 404 so that the tensioned member 210a-210b contacts equal percentages of the perimeters of the guide pulleys 406-408. As another example, the tensioned member 210a-210b contacts about 75% of the perimeter of the drive pulley 404 in FIG. 4, but other percentages could be contacted. For instance, in other embodiments, the guide pulleys 406-408 can be separated by a larger distance, and the drive pulley 404 can be positioned partially between the guide pulleys 406-408. In this embodiment, the tensioned member 210a-210b could contact less than 50% of the perimeter of the drive pulley 404, and the drive pulley 404 could operate to deflect the tensioned member as the tensioned member extends between the guide pulleys 406-408. In general, any suitable arrangement of pulleys could be used in the motor assembly 400.

Moreover, the tensioned member 210a-210b is shown in FIG. 4 as being smooth, and the pulleys 404-408 are shown in FIG. 4 as having smooth recesses for receiving the tensioned member 210a-210b. In other embodiments, the tensioned member 210a-210b could have an uneven surface, and/or the pulleys 404-408 could have uneven surfaces that contact the tensioned member 210a-210b. As a particular example, the pulleys 404-408 could have teethed surfaces that engage a corresponding surface of the tensioned member.

In addition, note that other mechanisms could be used to move a sensor head. The motor assembly 400 is provided here merely as an example of the numerous ways in which a sensor head can be propelled.

Figure 5:
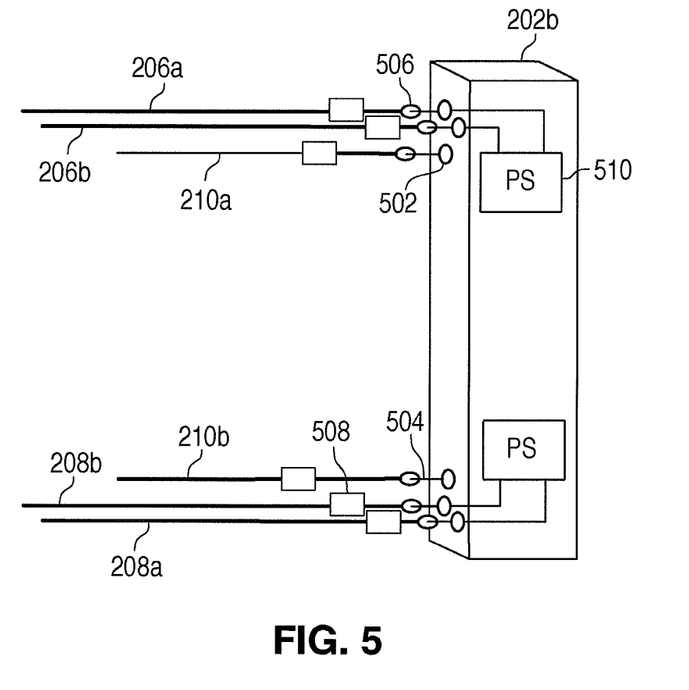
Figure 6:
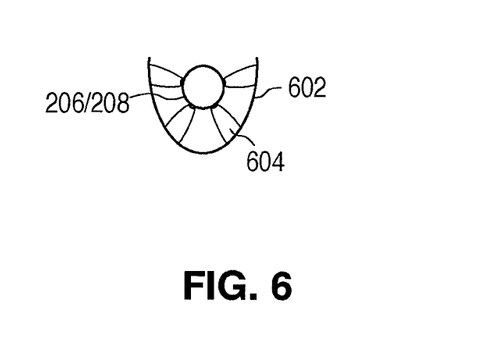

FIGS. 5 and 6 illustrate additional details of the frame of a scanner. As shown in FIG. 5, the support 202b includes various holes 502. Each hole 502 represents a different spot where a connector 504 can be placed for coupling to a rail or tensioned member. Each hole 502 clearly defines the position of a rail or tensioned member, and the holes 502 collectively define the spacings between the rails and tensioned members relative to each other. Each hole 502 could have any suitable size and shape.

Each connector 504 couples the support 202b to one end of a rail or tensioned member. For example, each connector 504 could include a smaller section that can fit through a hole 502 and a larger section that cannot. The smaller section could include a threaded member or other structure that can be tightened to apply tension on the associated rail or tensioned member. Each connector 504 includes any suitable structure for coupling to a cable or other rail or tensioned member. In this example, each connector 504 couples to a loop 506 formed at the end of a rail or tensioned member, although other mechanisms for coupling to a rail or tensioned member could be used. For instance, each connector 504 could connect directly to a rail or tensioned member, such as when the rail or tensioned member terminates with a "swageless" terminal.

Dampers 508 could be used in various places to help reduce vibrations on the rails and tensioned members. In this example, the dampers 508 are placed near the ends of the rails and tensioned members. However, the dampers 508 could be used in other locations, such as on the sensor heads. Each damper 508 includes any suitable structure for reducing vibrations.

Note that in FIG. 5, the connectors 504 could be used to apply tension on the rails and tensioned members. On the opposing support 202a, the rails and tensioned members may or may not be coupled to the support 202a by connectors that can apply tension on the rails and tensioned members. In some embodiments, for example, the rails and tensioned members can simply be attached to the support 202a, without using any devices that can apply tension to the rails and tensioned members.

As shown in FIG. 5, at least one power supply 510 provides operating power to the sensor head 204a-204b via the rails 206a-206b, 208a-208b. Each power supply 510 represents any suitable source of operating power for one or more sensor heads. A power supply 510 could, for example, represent at least one AC and/or DC voltage source(s). Power supplies with lower voltage levels can be used to comply with low-voltage directives for safety, or power supplies with higher voltage levels can be used to support lower current levels and less arcing damage through electrical contacts. In particular embodiments, each power supply 510 represents an AC power supply with an expected range of 20-40 VAC at 50-60 Hz or 24 VDC.

In this example, there are two rails 206a-206b or 208a-208b used to supply power to each sensor head 204a or 204b. In this embodiment, one rail 206a, 208a could be used as a voltage supply rail (DC) or as a voltage line #1 (AC), and the other rail 206b, 208b could be used as a voltage return rail (DC) or as a voltage line #2 (AC). However, more than two rails can be used to power each sensor head. For example, additional rails can be used to provide alternate voltage levels or types or to provide redundancy in the scanner.

FIG. 6 illustrates an example mechanism for covering a rail 206/208 (representing one of the rails 206a-206b, 208a-208b). In this example, the rail is partially covered by a U-shaped enclosure 602. The enclosure 602 is partially opened along at least one side, which allows an electrical contact 320 and/or a rail contact 322 to physically contact the rail. The enclosure 602 can be formed from insulative material(s) so that an electrical connection to the rail cannot be formed except along the opening of the enclosure 602. Spacers 604 within the enclosure 602 can contact the rail and help to maintain the position of the enclosure 602 on the rail. Any suitable number and type of spacers could be used.

The enclosure 602 can help to avoid inadvertent contact with and short-circuits across the rails 206a-206b, 208a-208b. For example, each rail could be slightly recessed within its associated enclosure 602. If a tool or other conductive object is dropped across the rails 206a-206b or 208a-208b, the enclosures 602 around the rails could help to avoid the creation of a short-circuit. Even if low voltages on the rails are used to power the sensor heads, a short-circuit condition could lead to the rebooting of control computers or other components. The use of insulative enclosures can help to avoid this.

Although FIGS. 2 through 6 illustrate one example of a scanner and related details for a paper machine or other system, various changes may be made to FIGS. 2 through 6. For example, as noted above, a scanner could include any number of sensor heads on one or multiple sides of a web. Also, various components in FIG. 3 could be combined, further subdivided, rearranged, or omitted and additional components could be added according to particular needs. As a particular example, it is possible to engage in low data-rate or other communications over the rails powering a sensor head. When a sensor head includes this functionality, the sensor head can include a transceiver supporting communications over one or more rails, and this transceiver can replace or supplement the wireless transceiver 310. In addition, the example structures shown in FIGS. 4 through 6 are possible implementations of portions of a scanner, although other implementations could also be used.

Figure 7:
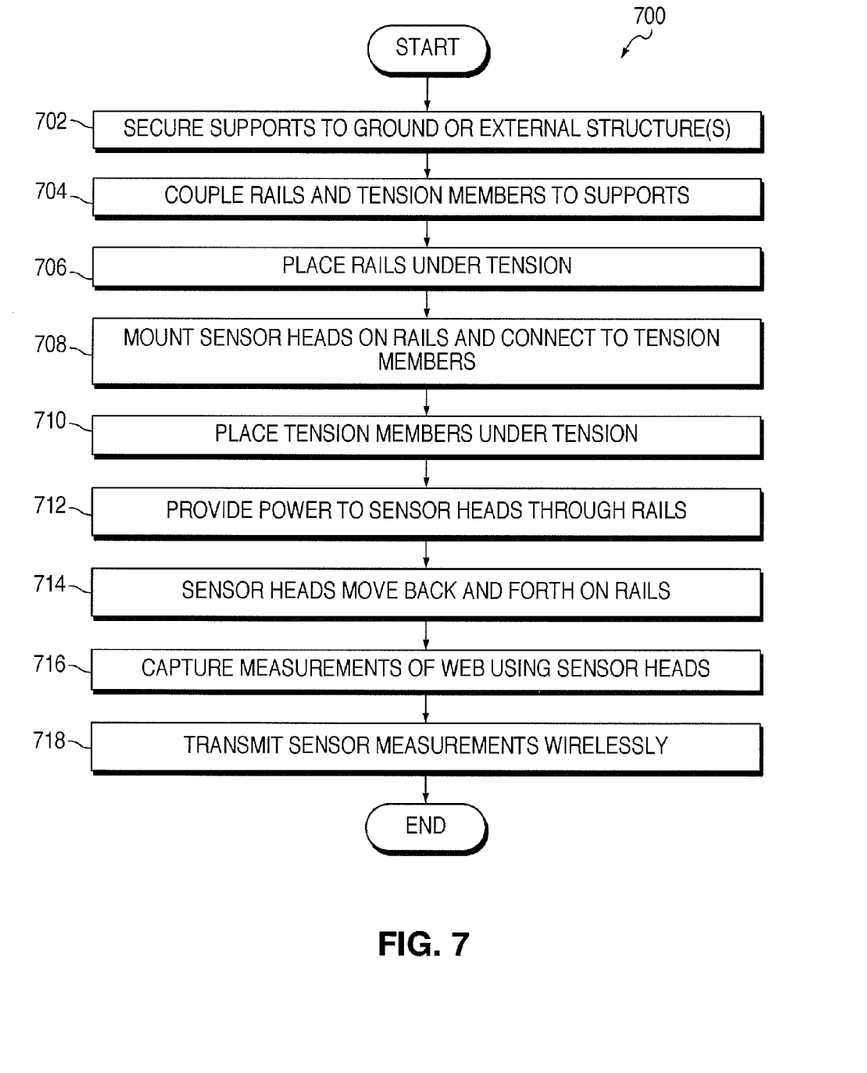
FIG. 7 illustrates an example method for using a scanner for a paper machine or other system according to this disclosure.

FIG. 7 illustrates an example method 700 for using a scanner for a paper machine or other system according to this disclosure. As shown in FIG. 7, supports for the scanner are secured in place to the ground or external structure(s) at step 702. This could include, for example, coupling the supports 202a-202b to the ground or to other structures within the paper machine 102. Rails and tension members are coupled to the supports at step 704. This could include, for example, coupling the rails 206a-206b, 208a-208b and the tension members 210a-210b to the supports 202a-202b in clearly defined locations. The rails are placed under tension at step 706. This could include, for example, using threaded connections in the connectors 504 or other mechanisms to place the rails 206a-206b, 208a-208b under suitable tension.

Sensor heads are placed on the rails and connected to the tension members at step 708. This could include, for example, mounting the sensor heads 204a-204b on their respective rails 206a-206b, 208a-208b. This could also include threading the tension members 210a-210b through the motor assemblies 400 of the sensor heads 204a-204b. Once connected, the tension members are placed under tension at step 710. This could include, for example, using threaded connections in the connectors 504 or other mechanisms to place the tension members 210a-210b under suitable tension.

Power is provided to the sensor heads over the rails at step 712. This could include, for example, using one or more power supplies 510 to provide voltages over the rails 206a-206b, 208a-208b. The power converters 306 in the sensor heads 204a-204b can receive this power and convert it into a suitable form for use in the sensor heads 204a-204b. The sensor heads move back and forth on the rails at step 714. This could include, for example, using the motors 316 in the sensor heads 204a-204b to pull on the tensioned members 210a-210b, moving the sensor heads back and forth. During this time, sensor measurements are captured using the sensor heads at step 716 and wirelessly transmitted at step 718. This could include, for example, the sensor(s) 304 providing sensor measurements to the signal processing circuitry 306, which provides sensor measurements directly to the transceiver 310 for transmission or to the controller 308 for further processing before transmission. During this time, the sensor heads can perform additional functions, such as temperature control, position tracking, or air compression and use.

Although FIG. 7 illustrates one example of a method 700 for using a scanner for a paper machine or other system, various changes may be made to FIG. 7. For example, FIG. 7 assumes that multiple sensor heads are used in a scanner, although a single sensor head could also be used. Also, while shown as a series of steps, various steps in FIG. 7 could overlap, occur in parallel, occur in a different order, or occur any number of times.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A system comprising:
   a frame comprising multiple separate supports and multiple flexible rails, each support configured to be secured in a position apart from another support, each flexible rail configured to be coupled to the supports and placed under tension; and
   a sensor head configured to be mounted on or to the rails and to move back and forth along the rails, the sensor head being substantially self-contained and comprising a motor configured to receive operating power over the rails as the sensor head moves back and forth along the rails, the motor configured to move the sensor head back and forth along the rails using the operating power.

2. The system of claim 1, further comprising:
a power supply coupled to the rails and configured to provide the power to the sensor head.

3. The system of claim 1, wherein each rail comprises an insulative enclosure leaving a portion of the rail exposed for electrical contact to the sensor head.

4. The system of claim 1, wherein the sensor head further comprises:
a chassis;
electrical contacts configured to form electrical connections to the rails;
a power converter/conditioner configured to receive the power from the rails via the electrical contacts and to at least one of: convert the power into a different form and condition the power;
one or more sensors configured to measure at least one characteristic of a material, the one or more sensors configured to operate using the power from the power converter/conditioner;
a wireless transceiver configured to wirelessly transmit sensor measurements from the one or more sensors; and
a motor controller configured to control the motor.

5. The system of claim 4, wherein the sensor head further comprises:
an air supply configured to compress and store air;
a temperature control unit configured to control a temperature of at least a portion of the sensor head;
one or more safety indicators configured to identify one or more conditions; and
a position sensor configured to identify a position of the sensor head.

6. The system of claim 1, wherein the sensor head does not push and pull any wiring assembly during movement along the rails.

7. The system of claim 1, wherein:
the frame comprises multiple sets of rails; and
the system comprises multiple sensor heads.

8. A system comprising:
a frame comprising multiple separate supports and multiple flexible rails, each support configured to be secured in a position apart from another support, each flexible rail configured to be coupled to the supports and placed under tension; and
a sensor head configured to be mounted on or to the rails and to move back and forth along the rails, the sensor head being substantially self-contained and configured to receive operating power over the rails;
wherein:
the frame further comprises a tensioned member configured to be coupled to the supports; and
the sensor head is configured to move back and forth using the tensioned member.

9. The system of claim 8, wherein:
the sensor head comprises a motor assembly having a motor and multiple pulleys or sprockets;
the pulleys or sprockets are configured to contact the tensioned member; and
the motor is configured to rotate at least one of the pulleys or sprockets to move the sensor head.

10. The system of claim 8, wherein the supports comprise multiple openings configured to receive connectors for coupling to the rails and tensioned member in specified locations.

11. The system of claim 8, wherein the tensioned member passes across the frame a single time and is secured at opposite ends to the supports.

12. The system of claim 8, wherein the sensor head is configured to receive the operating power over the rails while the sensor head is moving back and forth along the rails.

13. An apparatus comprising:
a scanner frame comprising multiple separate supports and multiple flexible rails;
each support configured to be secured in a position apart from another support;
each flexible rail configured to be coupled to the supports and placed under tension, the rails configured to receive a sensor head mounted on or to the rails and to supply operating power to a motor of the sensor head that is configured to move the sensor head back and forth along the rails using the operating power, the rails configured to supply the operating power to the motor as the sensor head moves back and forth along the rails.

14. The apparatus of claim 13, wherein each rail comprises an insulative enclosure leaving a portion of the rail exposed for electrical contact to the sensor head.

15. An apparatus comprising:
a scanner frame comprising multiple separate supports and multiple flexible rails;
each support configured to be secured in a position apart from another support;
each flexible rail configured to be coupled to the supports and placed under tension, the rails configured to receive a sensor head mounted on or to the rails and to supply operating power to the sensor head;
wherein the scanner frame further comprises a tensioned member configured to be coupled to the supports and to be connected to the sensor head so that the sensor head moves back and forth using the tensioned member.

16. The apparatus of claim 15, wherein the supports comprise multiple openings configured to receive connectors for coupling to the rails and tensioned member in specified locations.

17. The apparatus of claim 15, wherein the tensioned member passes across the frame a single time and is secured at opposite ends to the supports.

18. The apparatus of claim 15, wherein the rails are configured to supply the operating power to the sensor head while the sensor head is moving back and forth along the rails.

19. An apparatus comprising:
a sensor head configured to be mounted on or to rails of a scanner frame and to move back and forth along the rails;
the sensor head being substantially self-contained and comprising a motor configured to receive operating power over the rails as the sensor head moves back and forth along the rails, the motor configured to move the sensor head back and forth along the rails using the operating power.

20. The apparatus of claim 19, wherein the sensor head further comprises:
a chassis;
electrical contacts configured to form electrical connections to the rails;
a power converter/conditioner configured to receive the power from the rails via the electrical contacts and to at least one of: convert the power into a different form and condition the power;
one or more sensors configured to measure at least one characteristic of a material, the one or more sensors configured to operate using the power from the power converter/conditioner;

a wireless transceiver configured to wirelessly transmit sensor measurements from the one or more sensors; and a motor controller configured to control the motor.

21. The apparatus of claim 20, wherein the sensor head further comprises:

an air supply configured to compress and store air;

a temperature control unit configured to control a temperature of at least a portion of the sensor head;

one or more safety indicators configured to identify one or more conditions; and a position sensor configured to identify a position of the sensor head.

22. An apparatus comprising:

a sensor head configured to be mounted on or to rails of a scanner frame and to move back and forth along the rails, the sensor head being substantially self-contained and configured to receive operating power over the rails;

wherein:

the sensor head comprises a motor assembly having a motor and multiple pulleys or sprockets;

the pulleys or sprockets are configured to contact a tensioned member secured to the supports of the frame; and the motor is configured to rotate at least one of the pulleys or sprockets to move the sensor head.

23. The apparatus of claim 22, wherein the sensor head is configured to receive the operating power over the rails while the sensor head is moving back and forth along the rails.

* * * * *